United States Patent [19]

Gonzalez et al.

[11] Patent Number: 5,387,801
[45] Date of Patent: Feb. 7, 1995

[54] MULTIPLE WAVELENGTH LIGHT SOURCE

[75] Inventors: Ramon R. Gonzalez, Los Angeles; Alexander Waluszko, Pasadena, both of Calif.

[73] Assignee: UVP, Inc., San Gabriel, Calif.

[21] Appl. No.: 74,885

[22] Filed: Jun. 10, 1993

[51] Int. Cl.$^6$ ............................................. H05B 35/00
[52] U.S. Cl. .............. 250/504 R; 250/494.1; 362/231
[58] Field of Search ........... 250/504 R, 494.1, 492.1, 250/454.1, 455.1; 362/231

[56] References Cited

U.S. PATENT DOCUMENTS

| | | | |
|---|---|---|---|
| 2,117,754 | 5/1938 | Bell | 362/231 |
| 2,725,461 | 11/1955 | Amour | 362/231 |
| 4,000,407 | 12/1976 | Keller et al. | 240/103 R |
| 4,469,102 | 9/1984 | Fish | 250/494.1 |
| 4,657,655 | 4/1987 | Smoot et al. | 204/299 R |
| 4,712,014 | 12/1987 | Eich | 250/494.1 |
| 5,175,437 | 12/1992 | Waluszko | 250/504 R |

Primary Examiner—Jack I. Berman
Attorney, Agent, or Firm—Lyon & Lyon

[57] ABSTRACT

A UV transilluminator having three sets of tubes selectively providing ultraviolet light in the short, mid and long ranges. The sets of tubes are arranged in two rows with the upper row including alternating tubes of the first and second set. One of the first and second sets of tubes is transparent to UV radiation. The third set of tubes is arranged in the second row directly behind the transparent tubes of the other set. A filter overlies the sets of tubes with the transparent tubes located between the third set of tubes and the filter.

16 Claims, 4 Drawing Sheets

MULTIPLE WAVELENGTH LIGHT SOURCE

BACKGROUND OF THE INVENTION

The field of the present invention is lighting apparatus providing selectively varying wavelengths of light.

Ultraviolet light is electromagnetic radiation in the region of the spectrum located between X-rays and visible light. It is divided into three principal ranges: (1) UV-A, or longwave, (2) UV-B, or mid-range, and (3) UV-C, or shortwave. For each of these UV ranges, specific applications have been developed for its use and new applications are continuously being developed.

To obtain a desired ultraviolet wavelength, the fluorescent tube is most commonly used. The fluorescent tube is an electric discharge device that uses a low pressure mercury vapor arc to generate ultraviolet energy. The ultraviolet energy released in typical, commercially available fluorescent tubes is primarily at the wavelength of about 294 nanometers. In general, this ultraviolet energy is converted into other ultraviolet wavelengths by the use of phosphors which have the ability to absorb the ultraviolet energy and re-radiate it in other wavelengths. For example, longwave ultraviolet of about 365 nanometers and mid-range ultraviolet of about 300 nanometers are created by coating the inside of the fluorescent tubes with the proper phosphor(s) which converts the shortwave ultraviolet. The envelope of the tube is also typically made of a glass that inhibits the passage of the shortwave ultraviolet. To obtain a shortwave ultraviolet tube, a special glass which transmits about 254 nanometers is generally used, and no phosphor is required.

A common tool of those engaged in DNA research is the ultraviolet transilluminator. These devices provide up to three ultraviolet light sources to irradiate and/or visualize DNA patterns contained in gel matrices. Most commonly, transilluminators comprise a single set of ultraviolet lamps emitting one selected wavelength. In most such research, three separate wavelengths are used. Thus, it is common to use multiple such units in this work. At times, it may also be of value to employ a white light or other spectral selections such as, for example, the 420 nm and the 480 nm regions.

A conventional transilluminator having a single UV wavelength is disclosed in U.S. Pat. No. 4,657,655, incorporated herein by reference. An ultraviolet light apparatus having multiple wavelengths accomplished by rotation of a tube mounting mechanism is disclosed in U.S. Pat. No. 5,175,437, incorporated herein by reference.

SUMMARY OF THE INVENTION

The present invention is directed to a multiple wavelength light source having a plurality of tubes which are arranged to provide multiple wavelengths of light without mechanical intervention or substitution of devices.

In a first and separate aspect of the present invention, tubes generating different wavelengths of light are arranged in a housing with certain of the tubes positioned and arranged to transmit required wavelengths through other tubes, thus providing a compact illuminator.

In a second and separate aspect of the present invention, the foregoing tube arrangement is employed in an ultraviolet light transilluminator providing for a selection from multiple UV wavelengths.

In yet a further and separate aspect of the present invention, a compact illuminator includes alternating UV tubes of two selected wavelengths lying in a first plane with UV tubes of a third selected wavelength located directly behind tubes of one of the selected wavelengths positioned in the plane. In this way, alternate tubes in the plane can provide full illumination of either of the two wavelengths. The third set of tubes is located behind one set of tubes which is transparent. This location allows transmission to the opposite side of the two sets of tubes.

Accordingly, it is an object of the present invention to provide a multiple wavelength light source. Other and further objects and advantages will appear hereinafter.

DETAILED DESCRIPTION OF THE PREFERRED EMBODIMENT

Figure 1:
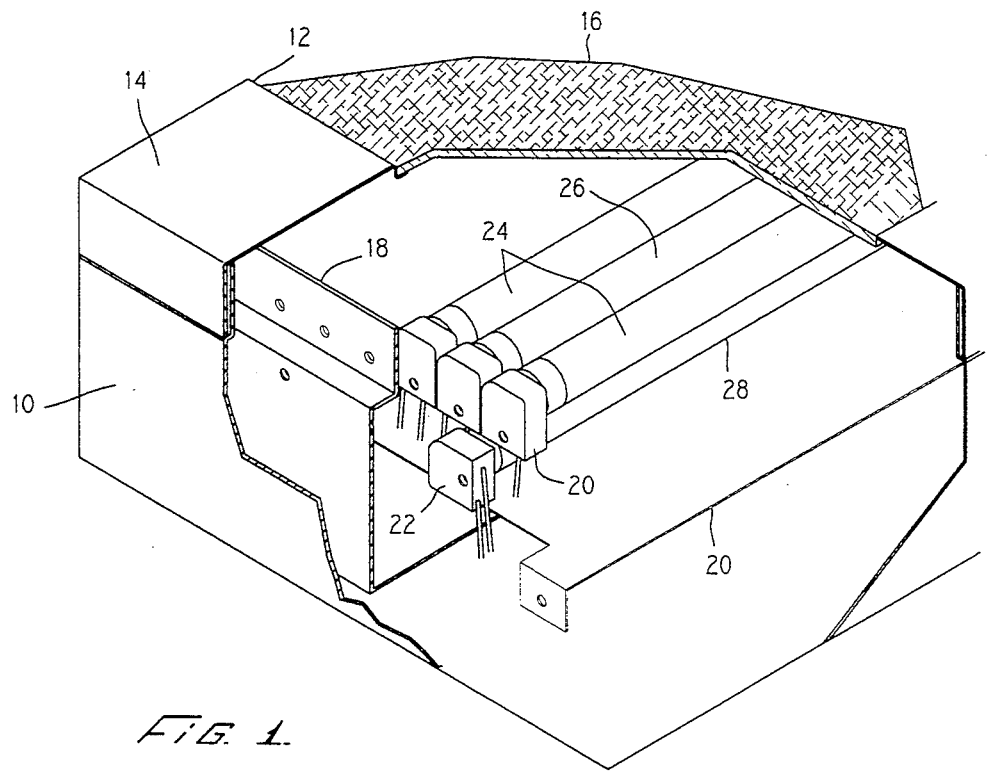
FIG. 1 is a perspective, partial view with a portion of the outer case and filter removed for clarity of a transilluminator.
Figure 2:
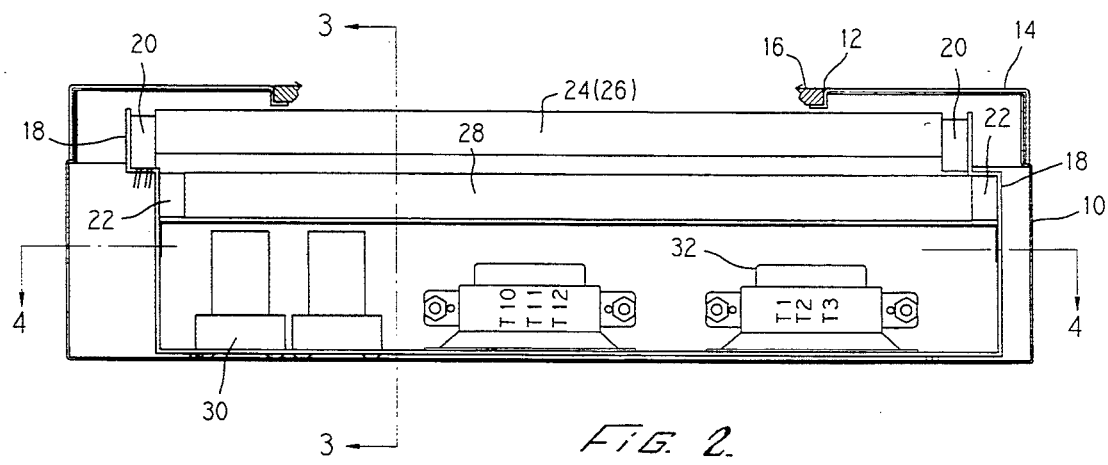
FIG. 2 is a side view with the wall of the housing removed of the transilluminator.

Turning in detail to the drawings, a housing 10, conveniently of sheet metal, provides a complete enclosure with a window 12 on the upper panel 14. A shortwave transmitting UV filter 16 is positioned in the window 12.

Mounted within the housing 10 are lamp holder brackets 18. The brackets 18 are to either side of the housing 10 and mount a reflector 20. The reflector 20 divides the housing into an upper lamp area and a lower component area. In the upper lamp area, the lamp holder brackets 18 retain two rows of lamp holders 20 and 22. The upper row of lamp holders 20 receives middle wavelength tubes 24 and short wavelength tubes 26. The middle wavelength tubes have a wavelength of 300 nanometers. These tubes 24 typically include a fluorescent coating as a mechanism for generating the appropriate light wavelength. The short wavelength tubes 26 have a selected wavelength of 254 nanometers which is generated by the source and transmitted through a tube which is transparent to ultraviolet radiation. A quartz glass tube may be employed. The middle wavelength tubes 24 and short wavelength tubes 26 are arranged to alternate in the plane of the upper row. The tubes are substantially parallel and extend, in both directions, across the width of the window 12.

Positioned in the lamp holders 22 in the lower row are long wavelength tubes 28. These long wavelength tubes 28 may use fluorescent coatings to generate the appropriate wavelength of 365 nanometers. The long wavelength tubes 28 are spaced apart and are positioned with the short wavelength tubes 26 directly between the long wavelength tubes 28 and the window 12 having the filter 16. Ultraviolet light generated by the long wavelength tubes 28 is able to pass through the short wavelength tubes 26 to the filter 16. The long wavelength tubes 28 in the lower plane are placed close enough to the upper plane that light generated by the long wavelength tubes 28 can be transmitted around the middle wavelength tubes 24 to fully illuminate the filter 16. In this way, tubes of three different wavelengths can be arranged to impinge upon the filter without requiring an expanded window width. The long and middle wavelength tubes may also be interchanged to the same effect.

Figure 3:
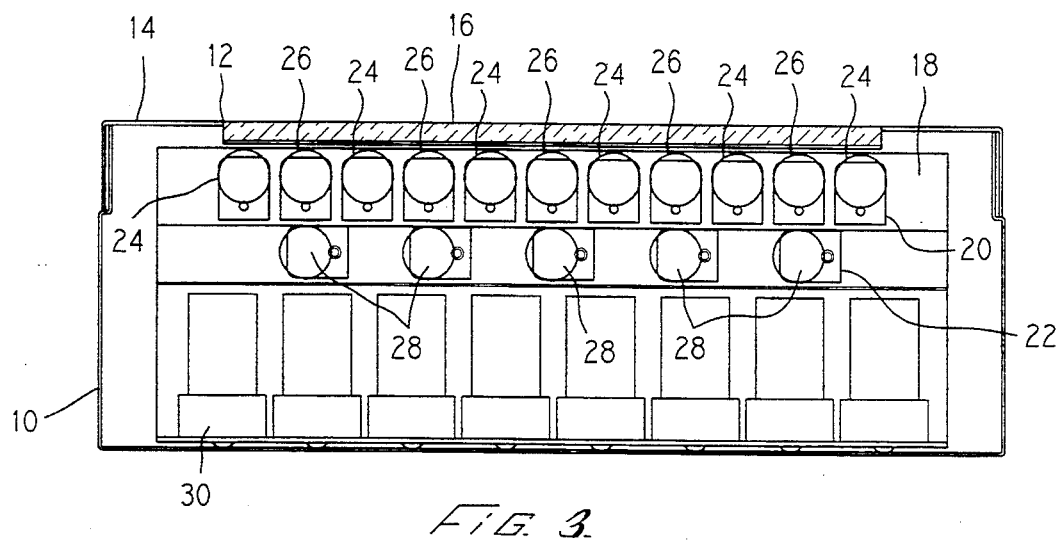
FIG. 3 is a cross-sectional end view taken along line 3—3 of FIG. 2.
Figure 6:
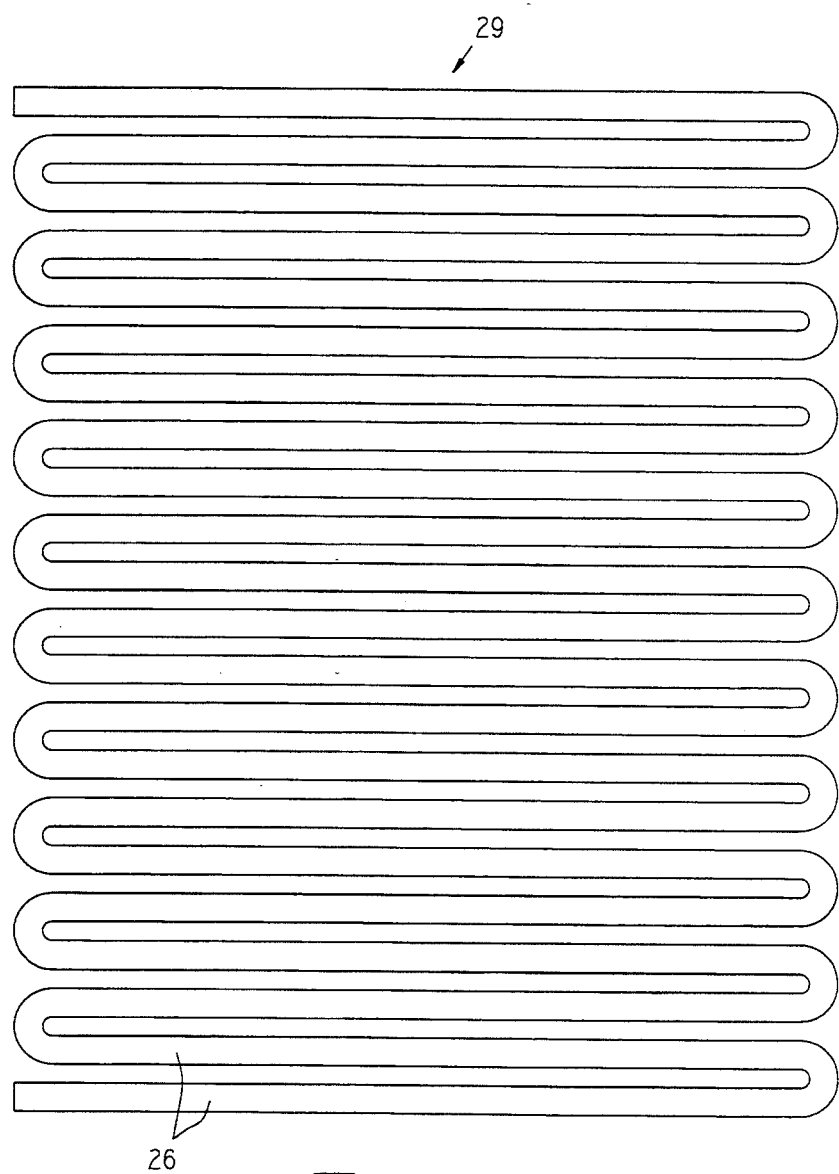
FIG. 6 is a plan view of a tube grid.
Figure 4:
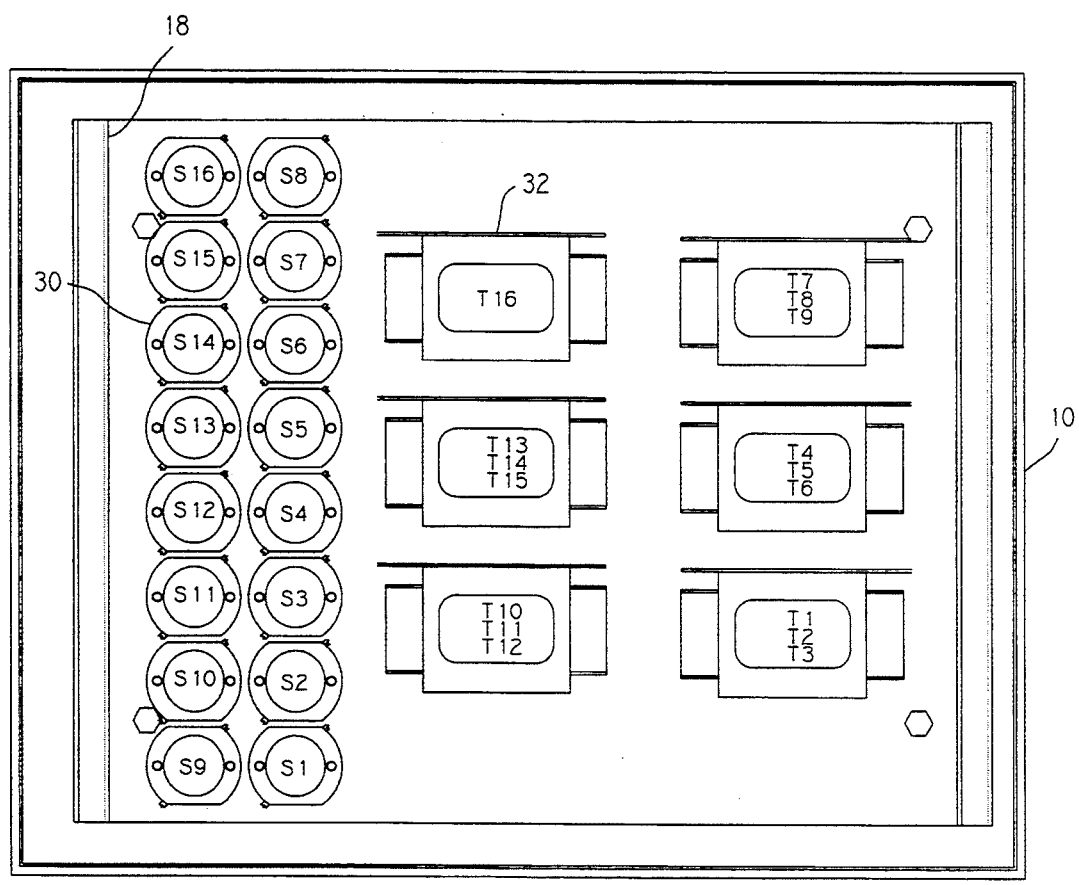
FIG. 4 is a cross-sectional plan view taken along line 4—4 of FIG. 2 of the transilluminator.

Several tube configurations are possible. For example, a grid may form the tubes. Such a grid 29 is illustrated in FIG. 6. Using such a device for the short wavelength tubes 26 permits an arrangement with the grid 29 above the florescent tubes 24 and 28 which would, in turn, be arranged in a lower plane. Alternatively, the long or middle wave tubes may be in the form of a grid. In this instance, the upper level would be as shown in FIG. 3 and the lower level would employ the grid.

Figure 5:
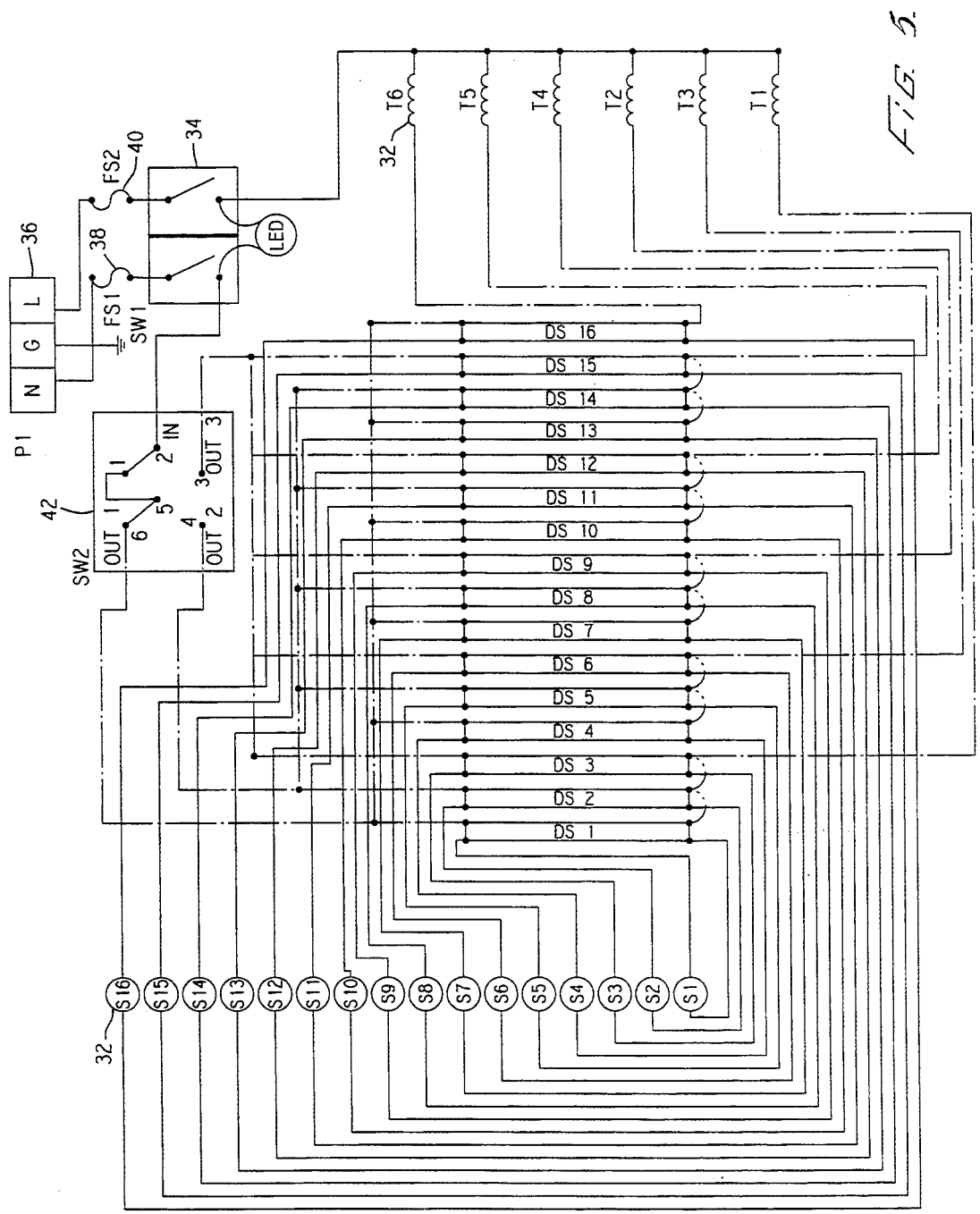
FIG. 5 is a schematic circuit diagram of the transilluminator.

Located below the reflector 20 in the lower component area are starters 30 and ballasts 32. These are coupled in a conventional manner with the tubes 24, 26 and 28 as can best be seen in FIG. 5. Electronic ballasts may also replace the conventional starters 30 and ballasts 32. The circuit also includes a switch 34 associated with a plug 36 through fuses 38 and 40. A wave selecting switch 42 allows choice of the appropriate viewing wavelength.

Accordingly, a three wavelength UV transilluminator is disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A multiple wavelength light source comprising
a housing having a window;
first tubes fixed in said housing in a first plane across said window;
second tubes fixed in said housing in a second plane parallel to said first plane with said first plane between said second plane and said window, said second tubes having a different selected wavelength than each said first tubes, said selected wavelength of said second tubes being 365 nm.

2. A multiple wavelength light source comprising
a housing having a window;
first tubes fixed in said housing in a first plane across said window;
second tubes fixed in said housing in a second plane parallel to said first plane with said first plane between said second plane and said window, said second tubes having a different selected wavelength than each said first tubes, said first tubes including first wavelength tubes and second wavelength tubes positioned alternately in said first plane.

3. The multiple wavelength light source of claim 2 wherein said first wavelength tubes have a selected wavelength of 300 nm, said second wavelength tubes have a selected wavelength of 254 nm and said second tubes have a selected wavelength of 365 nm.

4. The multiple wavelength light source of claim 3 wherein said second wavelength tubes are directly between said second tubes and said window, respectively.

5. A multiple wavelength light source comprising
a housing having a window;
first tubes fixed in said housing in a first plane across said window;
second tubes fixed in said housing in a second plane parallel to said first plane with said first plane between said second plane and said window, each said second tube being spaced one from another in said second plane and being positioned with a said first tube directly between said second tube and said window, respectively, each said first tube positioned directly between a said second tube and said window including a glass transparent to selected radiation from said second tube, respectively.

6. The multiple wavelength light source of claim 5 wherein said first tubes include first wavelength tubes and second wavelength tubes positioned alternately in said first plane, each said second wavelength tube being positioned directly between a said second tube and said window, respectively.

7. The multiple wavelength light source of claim 6, each of said first wavelength tubes having a different selected wavelength than said second wavelength tubes and said second tubes, said second wavelength tubes having a different selected wavelength than said second tubes.

8. A multiple wavelength light source comprising
a housing having a window;
first tubes fixed in said light box in a first plane across said window, said first tubes including first wavelength tubes and second wavelength tubes positioned alternately in said first plane;
second tubes fixed in said housing in a second plane parallel to said first plane with said first plane between said second plane and said opening, said second tube being spaced one from another in said second plane and being positioned with a said second wavelength tube directly between said second tube and said window, respectively, each said second wavelength tube including a glass transparent to selected radiation from said second tube, respectively, said first wavelength tubes having a selected wavelength of 300 nm, said second wavelength tubes having a selected wavelength of 254 nm and said second tubes having a selected wavelength of 365 nm.

9. A multiple wavelength light source comprising
a housing having a window;
first wavelength tubes fixed in said housing in a first plane across said window;
second wavelength tubes fixed in said housing in said first plane and positioned alternately with said first wavelength tubes;
third wavelength tubes fixed in said light box in a second plane parallel to said first plane with said first plane between said second plane and said window.

10. The multiple wavelength light source of claim 9 wherein said first wavelength tubes have a selected wavelength of 300 nm, said second wavelength tubes have a selected wavelength of 254 nm and said third wavelength tubes have a selected wavelength of 365 nm.

11. The multiple wavelength light source of claim 9 wherein said second wavelength tubes are positioned directly between said third wavelength tubes and said window, respectively.

12. The multiple wavelength light source of claim 11 wherein each said second wavelength tube includes a glass transparent to selected radiation from said third wavelength tube, respectively.

13. The multiple wavelength light source of claim 9 further comprising a light filter in said window.

14. An ultraviolet light source comprising first, second and third wavelength tubes, said first and second wavelength tubes alternating In a first plane, each said third wavelength tube being positioned behind a said second wavelength tube, respectively, to lie in a second plane parallel to said first plane, said second wavelength tube being substantially transparent to a selected wavelength of said third wavelength tube;

a filter substantially parallel to said first and second planes and positioned with said first plane between said filter and said second plane.

15. The ultraviolet light source of claim 14 wherein said first wavelength tubes have a selected wavelength of 300 nm, said second wavelength tubes have a selected wavelength of 254 nm and said third wavelength tubes have a selected wavelength of 365 nm.

16. The ultraviolet light source of claim 14 further comprising at least three circuits each having a switch, at least one starter and at least one transformer, said circuits including a first circuit for a plurality of said first wavelength tubes, a second circuit for a plurality of said second wavelength tubes and a third circuit for a plurality of said third wavelength tubes.

* * * * *